US006387877B1

(12) United States Patent
More et al.

(10) Patent No.: US 6,387,877 B1
(45) Date of Patent: May 14, 2002

(54) PURIFICATION METHOD

(75) Inventors: John Edward More; Jacqueline Rott; David Roger Lewin, all of Elstree (GB)

(73) Assignee: National Blood Authority (GB)

( * ) Notice: Subject to any disclaimer, the term of this patent is extended or adjusted under 35 U.S.C. 154(b) by 0 days.

(21) Appl. No.: 09/142,348

(22) PCT Filed: Mar. 7, 1997

(86) PCT No.: PCT/GB97/00642

§ 371 Date: Jan. 25, 1999

§ 102(e) Date: Jan. 25, 1999

(87) PCT Pub. No.: WO97/32893

PCT Pub. Date: Sep. 12, 1997

(30) Foreign Application Priority Data

Mar. 8, 1996 (DE) ............................................. 9604921

(51) Int. Cl.$^7$ ........................ A61K 38/16; A61K 31/74; C07K 14/00
(52) U.S. Cl. ................. 514/8; 514/2; 530/384; 530/395; 530/412; 530/414; 530/416; 530/417; 530/427; 530/829; 530/831; 424/78.1; 424/78.11
(58) Field of Search ........................ 514/8, 2; 530/384, 530/395, 412, 414, 416, 417, 427, 829, 831; 424/78.1, 78.11

(56) References Cited

U.S. PATENT DOCUMENTS 3,998,946 A  12/1976  Condie et al. ................. 424/35

FOREIGN PATENT DOCUMENTS

| WO | WO 95/07703 | * | 3/1995 |
| WO | 95/22556 |   | 8/1995 |

OTHER PUBLICATIONS

Libert et al., *J. Exp. Med.*, vol. 180, pp. 1571–1575, Oct. 1994.*
Hao et al., *Biochemica et Biophysica Acta*, (p) 322 (1), pp. 99–108, Sep. 1973.*
Bouften et al., *European Journal of Immunology*, vol. 22, No. 10, pp. 2687–2695, Oct. 1992.*
Edwards et al., *International Journal Vox Sanguinis of Transfusion Medicine*, vol. 52, pp. 53–59, 1987.*
Weary, M., "Depyrogenation", on *PYROGENS: Endotoxins, LAL Testing, and Depyrogenation*, Frederick C. Pearson, III, ed., Marcel Dekker, Inc., 203–218 (1985).
Libert, C., et al., "Protection by $\alpha_1$–acid Glycoprotein Against Tumor Necrosis Factor–induced Lethality", *J. Exp. Med.*, 180, 1571–1575, (Oct. 1994).
Pentel, P.R., et al., "Effects of High Dose Alpha–1–Acid Glycoprotein on Despiramine Toxicity in Rats", *Journal of Pharmacology and Experimental Therapeutics*, 246 (3), 1061–1066, (1988).
Boutten, A., et al., "$\alpha_1$–Acid Glycoprotein Potentiates Lipopolysaccharide–induced Secretion of Interleukin–1 $\beta$, Interleukin–6 and Tumor Necrosis Factor–$\alpha$ by Human Monocytes and Alveolar and Peritoneal Macrophages", *European Journal of Immunology*, 22 (10), pp. 2687–2695, (Oct. 1992).
Chen, R.F., "Removal of Fatty Acids from Serum Albumin by Charcoal Treatment", *The Journal of Biological Chemistry*, 242 (2), pp. 173–181, (Jan. 25, 1967).
Edwards, C.A., et al., "Tri (n–Butyl) Phosphate/Detergent Treatment of Licensed Therapeutic and Experimental Blood Derivatives[1]", *International Journal Vox Sanguinis of Transfusion Medicine*, 52, pp. 53–59, (1987).
Hao, Y., et al., "Development of Large–Scale Fractionation Methods IV. A Simple Method For the Large–Scale Preparation of $\alpha_1$–Acid Glycoprotein", *Biochimica Et Biophysica Acta* (P) , 322 (1), pp. 99–108, (Sep. 21, 1973).
Kistler, P., et al., "Large Scale Production of Human Plasma Fractions", *Vox Sanguinis*, 7, pp. 414–424, (1962).

* cited by examiner

Primary Examiner—Christopher S. F. Low
Assistant Examiner—Abdel A. Mohamed
(74) Attorney, Agent, or Firm—Schwegman, Lundberg, Woessner & Kluth, P.A.

(57) ABSTRACT

The invention relates to a method of removing endotoxin from preparations of alpha-1-acid glycoprotein (orosomucoid) by contact with a finely divided non-toxic resin such as fumed silica. The invention also relates to a purification process for alpha-1-acid glycoprotein which includes this deprogenation step, and to the depyrogenated product and its clinical uses.

17 Claims, 2 Drawing Sheets

DIAGRAMATIC REPRESENTATION OF A TYPICAL CHROMATOGRAPHIC PROFILE

ABSORBANCE PROFILE (——) ELUTION BUFFER CONCENTRATION (······)

PURIFICATION METHOD

FIELD OF THE INVENTION

The present invention relates to an improved method for the purification of alpha-1-acid glycoprotein, and to therapeutic uses of highly purified alpha-1-acid glycoprotein.

BACKGROUND OF THE INVENTION

Alpha-1-acid glycoprotein (AAG) is a plasma glycoprotein of approximate molecular weight 41 kD. It is an acute phase protein, present in plasma at a concentration of between 0.5–1 g/l in healthy people, rising in disease states, particularly inflammatory diseases, to levels up to about 2 g/l.

The physiological role of AAG is poorly understood. As an acute phase protein, its serum level increases in response to a number of stresses and insults including infection, trauma, burns, etc. AAG is known to act on a wide variety of cells and it has been suggested that AAG may play a role in the immune response. In addition, AAG has been shown to bind to a diversity of drugs, particularly basic and lipophilic drugs. Therapeutic uses of AAG based on this latter aspect have been suggested in the literature but none have been actually developed as far as the clinic.

We believe that one reason for this is the relatively high level of contaminants which remain even in so-called highly purified preparations. The endotoxin lipopolysaccharide (LPS) derived from bacterial cell walls, also known as pyrogen, is one such contaminant.

LPS is the causative agent of septic shock, which is a major cause of morbidity following gram-negative bacterial infection, particularly in hospitalised and immunocompromised patients. The presence of LPS in AAG preparations renders them unsuitable for human therapy.

Currently available methods of purifying AAG are laborious and time consuming, involving a large number of individual steps. Furthermore, they are unsuitable for large scale preparative processes. One such technique is described by Hao and Wickerhauser (Biochem. Biophys. Acta, 322, 99–108 (1973)). This involves adsorption and elution of a Cohn Fraction V supernatant from DEAE Sephadex, concentration, dialysis, adsorption and elution from carboxymethylcellulose, dialysis and finally freeze drying. With both dialysis steps taking 48 hours each, the whole process takes over a week. Furthermore, despite Hao and Wickerhauser's suggestion to the contrary, the technique is not amenable to scale up for the treatment of the volumes of starting material handled by commercial manufacturers (typically several batches per week of up to 10,000 1 per batch of Cohn Fraction V supernatant). Most importantly this process has not been able to reduce the levels of bound contaminating LPS to levels acceptable for clinical use.

Other prior processes for purifying AAG have not been successful in depleting LPS from AAG preparations to levels which are acceptable for clinical use. One such method involves adsorption and elution of AAG preparations from Detoxigel resins (Boutten et al Eur. J. Immunol. 22, 2687–2695 (1992)). The purpose of this method was to ensure LPS was depleted from an AAG preparation for use in in vitro studies examining the effects of added LPS on cytokine production. This chromatography medium is not however suitable for use in preparing products for human administration, and in any event, LPS levels were only reduced to 200 pg/mg (approx. 2 EU/mg) of protein (EU= endotoxin units). This level is still too high for products intended for human use, particularly at the AAG doses likely to be required clinically (for example from 10 g to 30 g per dose) e.g. in the treatment of drug toxicity.

SUMMARY OF THE INVENTION

We have now developed a new process for removing LPS from an AAG containing preparation.

Thus in its broadest aspect, the present invention provides a method of removing LPS from an AAG containing preparation comprising contacting said preparation with a finely divided non-toxic resin.

In this way, it is possible to deplete LPS from AAG containing preparations to levels which are compatible with therapeutic uses of the preparations.

Preferred resins are non-substituted resins.

Preferably, said resin is a particulate resin, especially an inorganic particulate resin and more preferably a hydrophilic resin. Resins with porous surfaces for example silane-based resins such as fumed silica are particularly suitable. One such fumed silica resin which may be used in the method of the invention is the commercially available fumed silica product AEROSIL™ fumed silica (Degussa AG, Frankfurt), which has siloxane and silanol groups on the surface of the particles.

AEROSIL™ fumed silica and similar resins have previously been used in the pharmaceutical industry both as a component, for example in the formulation of tablets and ointments, and also in purification processes such as the removal of lipid and lipid-like substances, and lipoprotein from plasma and plasma derived products. We are not aware of any previous suggestion to use AEROSIL™ fumed silica, or any other finely divided particulate resin as a depyrogenating agent for AAG. The non-toxic nature of AEROSIL™ fumed silica represents a distinct advantage over prior methods of purifying AAG which rely on separation techniques using materials which are not suitable for therapeutic applications.

For use in the process of the invention, the particles may have a high surface to weight ratio such as from 1 $m^2/g$ to 1000 $m^2/g$, preferably from 50 $m^2/g$ to 700 $m^2/g$, and more preferably from 330 $m^2/g$ to 430 $m^2/g$, such as 380 $m^2/g$.

We have also developed a new simple purification method for AAG which includes our new depyrogenation step and which produces a depyrogenated AAG preparation suitable for clinical use. The new purification method accordingly overcomes the aforementioned disadvantages associated with prior AAG purification processes.

Thus in another aspect, the present invention provides a method of purifying AAG comprising contacting an AAG-containing preparation with an anion exchange matrix, eluting an AAG-enriched fraction from said matrix and depyrogenating an AAG-enriched fraction by contact with a finely divided non-toxic particulate resin followed by elution of an LPS-depleted AAG fraction.

Using such a technique, AAG preparations containing as little as 0.016 EU/mg AAG protein can be obtained.

DETAILED DESCRIPTION OF THE INVENTION

A variety of AAG containing starting materials may be used, for example plasma, cryosupernatant, and plasma fractions for example Cohn Fraction V supernatant and Cohn Fraction IV supernatant. In the case of recombinant AAG production, the technique may also be used on cell cultures and cell culture supernatants and fractions thereof.

For reasons of economy, Fraction V supernatant is a preferred starting material, since this enables maximum usage of donated plasma, the fraction essentially being a waste product in the purification of albumin, and being particularly rich in AAG. Fraction V supernatant typically contains 40% ethanol, 10 mM citrate, 50 mM acetate pH 4.8. It has a low protein content (<2 g/l); 80% of the UV absorbing material (OD280) has a molecular weight <10,000 daltons. AAG has a relatively low molecular weight and is extremely soluble; it does not precipitate during the Cold Ethanol Fractionation Process hence the majority (~60 to 80%) is found in solution in Fraction V supernatant. Typical AAG concentrations in Cohn Fraction V supernatant will be in the range 0.2 to 0.35 g/l.

Any conventional anion exchanger may be used, provided, of course, that it has the ability to bind AAG. Examples include inert substrates such as agarose, for example Sepharose carrying functional groups having the ability to bind AAG such as positively charged groups for example diethylaminoethyl (DEAE), diethyl-(2-hydroxypropyl)-aminoethyl (QAE) and quaternary ammonium (Q). High capacity resins are preferred, and preferably resins of larger particle size, in the range 100 to 300 $\mu$m. The increased bed stability of large beads is of advantage in treating viscous materials such as Fraction V supernatant allowing minimal back pressure when the process is carried out by column chromatography; furthermore, AAG-containing fractions can be rapidly removed, maximising AAG recovery and reducing the process time. Preferred matrices include Q-Sepharose Big Bead, Q Hyper D and Toyopearl Super Q. All have high capacities for AAG.

The AAG containing starting material may conveniently be contacted with the anion exchanger in the presence of an ethanolic solution of concentration from 30 to 45% preferably 35 to 45%, more preferably at about 40%, at the pH of fraction V supernatants, about pH 4.5 to 5.5, no adjustment being required, and at temperatures in the range of 2° to 30° C., preferably 5 to 15° C. and more preferably about 10° C.

The anion exchange matrix may be provided either as batch or column form, the latter being preferred for both speed and convenience.

Generally, the matrix is used in a ratio of AAG-containing material to matrix from 1000:1 to 5:1 conveniently about 200:1 (by volume).

In operating the method as a column, the anion exchange medium will normally be packed into the column and then equilibrated with a relatively low ionic strength buffer at a pH in the range 4.0 to 5.5, preferably 4.0 to 4.8 and more preferably about 4.1. A useful buffer is acetate buffer, for example sodium acetate of concentration 0.02 M to 0.2 M preferably 0.1 M to 0.13 M and more preferably about 0.13 M.

After loading the AAG containing material onto the column non-bound proteins may be removed by washing with a low ionic strength buffer for example the buffer used to pre-equilibrate the column.

AAG may then be eluted in a variety of ways. One such way is by means of increasing ionic strength buffers based on the equilibration buffer. Generally, the electrolyte is sodium chloride, but other salts may be used for example sodium acetate. AAG may be eluted either by means of a linear salt gradient or by a stepwise increase in salt concentration, from 0 to saturated (>3M) sodium chloride, preferably 0 to 1.0 M and more preferably gradients of 0–0.2 M. A useful buffer for eluting AAG is 0.13 M sodium acetate 0.2 M sodium chloride pH 4.1.

In an alternative method, AAG may be eluted by decreasing the pH of the buffer to below pH 4.1, for example by adding appropriate buffers such as 0.1 M sodium phosphate, at a pH in the range 2.0–3.0.

The AAG enriched preparation is then neutralised with sodium hydroxide prior to depyrogenation according to the invention and as described below.

Depyrogenation with finely divided particles as described previously may be carried out conveniently as a batch process, using equipment which has been depyrogenated according to conventional methods for example soaking in alkali such as 0.5 M NaOH for at least one hour or by heating at temperatures above 200° C. for greater than one hour.

Generally, the partially purified AAG preparation will be contacted with the particles for upwards of 15 minutes to an overnight contact time, e.g. for several hours e.g. 2 hours and generally for about 1 hour, at temperatures of between 4° to 70° C., preferably 40 to 37° C. and more preferably about 20° C.

The particles may be used in a weight:weight ratio of particles to AAG protein of from 50:1 to 0.2:1 (by weight), preferably from 5:1 to 0.1:1 preferably 2:1 to 1:1 and more preferably 1:1 with AAG being in solution at a concentration of 0.1 g/l to 250 g/l preferably 2 to 50 g/l and more preferably about 3 g/l.

The AAG preparation may be concentrated for therapeutic use using conventional methods including ultrafiltration or freeze drying. Ultrafiltration (UF) may conveniently be carried out using a 10 kD UF cassette (ie. a filter which has a 10,000 dalton molecular weight cut off) using tangential flow, to reach a concentration in the range 10 to 250 g/l, conveniently 100 g/l.

Depyrogenation may take place either before or after this concentration step, however we have found that concentration after depyrogenation is preferred as it reduces losses of AAG at depyrogenation and improves yields.

To further process the purified AAG into a form suitable for therapeutic use, the preparation may be diafiltered into an appropriate buffer suitable for human administration, for example phosphate buffered saline at pH 7.5.

The AAG preparation may be subjected to a range of viral inactivation steps, which are now a mandatory requirement in most countries for blood and plasma derived products. We have found that AAG purified according to the process of the invention is stable to prolonged heating at high temperatures. Thus a preferred viral inactivation step comprises heating the purified AAG in solution at pasteurisation temperatures of from 58° C. to 70° C. for at least 2 hours, preferably for about 10 hours, optionally in the presence of recognized stabilisers such as salts, amino acids or sugars examples of which include sodium chloride, glycine and sucrose, although stabilisers are not absolutely required for such AAG preparations.

Compared to the majority of proteins, AAG is a relatively small molecule; thus another method of eliminating viruses from an AAG containing preparation according to the invention is virus filtration, through filters of pore size <50 nm, preferably 15 nm.

Current recommendations from the Committee for proprietary medicinal products European Commission are for two independent virus inactivation/elimination steps for intravenous products made from plasma. Both of these methods can be used sequentially for treating the AAG preparations according to the invention. Other methods which can be used include solvent detergent treatment e.g.

as described in Edwards et al., Vox. Sang. 52, 53–59 (1987) and heat treatment of freeze-dried AAG preparations according to the invention.

By using the process of the invention, we have been able to purify AAG from Fraction V supernatant with an average yield of up to 80% and purity of >98% as measured by cellulose acetate electrophoresis. Furthermore, using this method it is possible to produce, for the first time, substantially depyrogenated AAG preparations having a LPS concentration of less than 0.1 Eu/mg protein, which passes the European Pharmacopoeia animal pyrogenicity test for substances of this kind.

Thus viewed from a further aspect, the present invention provides AAG substantially free of LPS, said AAG having a LPS concentration of less than or equal to 0.1 Eu/mg AAG, preferably less than 0.075 Eu/mg and more preferably less than 0.050 Eu/mg and especially preferably less than 0.02 Eu/mg. Such an AAG preparation substantially depleted of LPS according to the invention is hereinafter referred to as Apo-AAG.

According to a further aspect, the present invention provides a virus inactivated or depleted Apo-AAG preparation. Inactivation may be carried out by methods including the aforementioned solvent detergent treatment, or pasteurisation, and depletion methods include the aforementioned virus filtration.

According to a yet further aspect, the present invention provides Apo-AAG according to the invention for use in therapy.

AAG is known to have useful drug binding properties, and our new highly purified Apo-AAG is particularly useful in the clinical management of drug overdoses, for example in the case of tricyclic anti-depressants where overdose can be lethal.

Thus viewed from a further aspect, the present invention provides a method of treating drug toxicity comprising administering to a patient in need of such treatment an effective amount of Apo-AAG.

In another aspect, the present invention provides the use of Apo-AAG in the manufacture of a medicament for use in the treatment of drug toxicity.

This aspect is particularly useful in treating toxic effects associated with overdoses of basic drugs such as quinine, lignocaine, propranolol and particularly tricyclic anti-depressants such as amitriptyline, desipramine and nortriptyline.

For therapy according to the invention, AAG may be formulated according to conventional methods of pharmacy, together with pharmaceutically acceptable excipients, carriers or diluents as, for example, described in Remingtons Pharmaceutical Sciences ed Gennaro, Mack Publishing Company, Pennsylvania USA (1990). Additional components such as preservatives may be used. AAG may be formulated into compositions for administration by any convenient route e.g. enterally or parenterally, by transmucosal delivery e.g. rectally, in implants or by intravenous, intramuscular or subcutaneous injection etc.

Viewed from a further aspect, the present invention provides a pharmaceutical composition comprising AAG together with one or more pharmaceutically acceptable carriers or excipients.

These compositions may for example take the form of solutions, emulsions, pessaries and suppositories, as well as other stabilised presentations such as freeze dried plugs, foams and glasses. The formulation may be chosen as appropriate to the route of administration which may be by all conventional methods including parenterally (e.g. intrperitoneally, subcuutaneously, intramuscularly, intradermally or intravenously or mucosally (e.g. orally, nasally, vaginally, rectally and via the intraocular route).

Actual treatment regimes or prophylactic regimes and dosages will depend to a large extent upon the individual patient and may be devised by the medical practitioner based on individual circumstances. Doses may be in the range of 10 to 30 g AAG.

BRIEF DESCRIPTION OF THE DRAWINGS

The invention will now be described by way of the following non-limiting Examples, with reference to the Figures which show.

Figure 1:
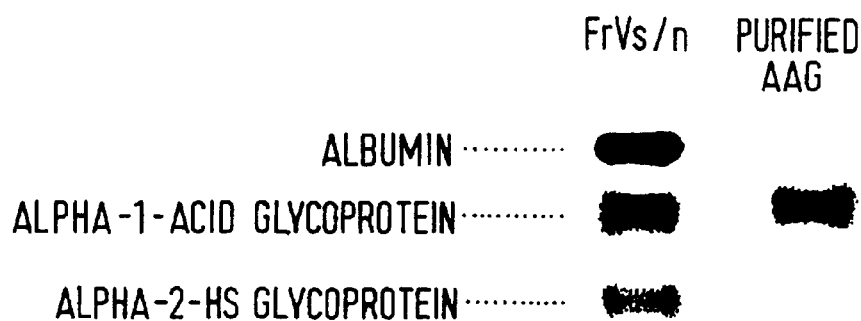
FIG. 1: A scanned image of an agarose gel showing AAG purified from a fraction V supernatant. The starting material and purified AAG are both shown.

In the following Examples, LPS was measured by the gel clot assay for endotoxins using Limulus Amoebocyte Lysate with Atlas Bioscan *E. Coli* endotoxin as a positive control.

This assay was carried out using purchased reagents and Water for Injection (WFI). A series of dilutions of the test material was prepared in duplicate by diluting with WFI. No adjustment of pH was necessary as samples are always in the range pH 6.5–7.5. Assays were performed in duplicate on: diluted test samples; a positive control (diluted Endotoxin Standard, as per European Pharmacopoeia Ph. Eur: V2.1.9.) and a negative control (WFI).

Assay Method

This was according to European Pharmacopoeia Ph. Eur: V2.1.9. 0.1 ml of diluted sample or control were added into a pyrogen free soda-glass tube containing 0.1 ml of lysate (previously validated) and the tube was shaken gently to mix. The tubes were incubated, uncapped, in a water bath at 37° C. for 1 hour.

The test was read by carefully inverting each tube through 180°. A positive test was recorded if the gel clot remained intact when the tube was inverted through 180°. The end point positives for the duplicates should be within one two-fold dilution of each other. Where the end point positives were not the same, the geometric mean was calculated by multiplying the endotoxin level in the end point positives and then taking the square root. Results were expressed as Eu/ml, converted to Eu/mg AAG using the protein concentration of the AAG solution.

The positive control (0.06 Eu/ml) and the negative control (WFI as the diluent) were tested with every run of samples. Where no clot formed in the positive control the quality of the lysate was checked using new lysate. Where this did not highlight poor lysate as the culprit of a negative result a new positive control was made up and tested, by the validation method.

The test sample at the lowest dilution that clots is equivalent to 0.06 Eu/ml and the result is 0.06×dilution factor. Samples were diluted according to the following series:

neat, 1/4, 1/8, 1/16, 1/32, 1/64, 1/128 and 1/256.

EXAMPLE 1A

Purification of Technical Grade Alpha-1-Acid Glycoprotein (AAG) form Fraction V Supernatant DEAE Sephadex A-50 gel, (Pharmacia), is supplied as a dry powder. 675 g of dry gel was swollen overnight in 100 litres of 0.25M sodium acetate (NaAc), pH unadjusted. After swelling the gel was batch equilibrated with 4 aliquots of 0.13M NaAc, pH 4.1, conductivity=1.85 mS/cm. The gel was drained after each aliquot. A total of 250 litres of equilibration buffer was used. Approximately 450 litres of Fraction V Supernatant, produced by the method of Kistler and Nitschmann plasma fractionation (Vox Sang, 7, 414–424, 1962), was added to the equilibrated gel and mixed for 90 minutes. The unbound protein solution was drained from the gel. The gel was washed with 4 aliquots of 0.13M NaAc, pH 4.1, conductivity=1.85 mS/cm. The resultant washed gel cake was batch eluted with 35 litres of 0.13M NaAc, 1M sodium chloride (NaCl), pH 4.1. This produced 41.8 kg of eluate solution. 3 litres of 1M Sodium Hydroxide (NaOH) was added to the eluate to achieve pH 6.4. The pH adjusted eluate was concentrated by ultrafiltration to 1 litre and then diafiltered against 4 litres of 10 mM sodium phosphate, pH 7.0. A final protein concentration of approximately 100 g/L was produced.

EXAMPLE 1B

Purification of Clinical Grade $\alpha_1$ Acid Glycoprotein (AAG) from Fraction V Supernatant Column Preparation Q Sepharose Big Bead (25.2 cm×19 cm–9.5 litres) was depyrogenated with 30 litres of 0.5M Sodium Hydroxide (NaOH) for 1 hour. The gel was equilibrated with 50 litres of 0.13 M Sodium Acetate (NaAc) pH 4.1.

Fraction V Supernatant Preparation

This was prepared according to the method of Kistler and Nitschmann, Vox Sang. 7, 414–424 (1962).

AAG Preparation 1.1 750 litres of Fraction V Supernatant was depth filtered at <0° C., warmed to 10° C., then loaded onto the gel at 2 litres per minute. After loading, the column was washed with 50 litres of 0.13M NaAc pH 4.1, to wash off the unbound protein.

1.2 AAG was eluted with 50 litres of 0.13M NaAc, 0.2M Sodium Chloride (NaCl) pH 4.1 at 2 litres per minute. The gel was cleaned with 50 litres of 0.13M NaAc, 1M NaCl pH 4.1 then 20 litres of 0.5M NaOH and stored in 10 mM NaOH.

1.3 The eluted AAG was neutralised with NaOH before sterile filtration.

1.4 The purification stage yielded 27.4 litres of 5.7 g/l AAG, a total of 156 g of AAG.

1.5 154 g of AAG was treated with 154 g of Aerosil 380 to remove pyrogens. After mixing for 2 hours at 20° C., the Aerosil was removed by filtration through glass fibre filters.

1.6 The depyrogenated AAG was concentrated to 120 g/l, by ultrafiltration using membranes with 10,000 molecular weight cut off. The concentrated solution was diafiltered against 4 litres of 10 mM sodium phosphate, 150 mM NaCl pH 7.5 (PBS).

1.7 Viral inactivation of the AAG concentrate was achieved by filtration through a virus filter with pore size of 15 nm. After sterile filling, virus inactivation of the product was achieved by pasteurisation for 10 hours at 60° C.

1.8 All processes were carried out under clean conditions, with all surfaces coming in contact with the product being depyrogenated with NaOH.

1.9 The starting material and the product were analyzed by agarose gel electrophoresis using pre-poured 1% agarose gels from Ciba Corning. Samples of 5–10 g/l Fraction V supernatant (which had been diafiltered into saline to remove salts and ethanol) and purified AAG were subjected to electrophoresis in 60 mM Barbitone buffer pH 8.6. FIG. 1 shows a Coomassie blue stained gel.

Using this method an AAG preparation having 0.016 EU/mg AAG was obtained.

EXAMPLE 2

Selection of Suitable Anion Exchange Resins for Use in Preparing AAG from Fraction V Supernatant for Subsequent Depyrogenation The high ethanol content (40%) makes Fraction V supernatant very difficult to process. This may be due to its high relative viscosity (2.8 at 20° C.)

The initial approach was to remove ethanol and concentrate by ultra filtration but the large volumes and low flux rates (due to ethanol) were found to make processing times extremely long. Instead chromatographic capture directly from Fraction V supernatant was chosen, ideally without modifying pH, or ethanol concentration. Most anion exchangers have very low capacity under these conditions and high back pressures allowing only low throughput and requiring large volumes of anion exchanger. Hence to improve process feasability an anion exchanger with good capacity (>10 g AAG/L gel) at high flow rates was sought.

Method

A wide range of anion exchange resins were selected, both Q and DEAE derivatives were investigated. Resins were packed into chromatographic columns at the manufacturers recommended flow rates. After equilibration in 0.13M NaAc pH 4.1, the resins were overloaded with Fraction V supernatant; flow rates had to be reduced with many of the gels due to excessive back pressure. Unbound proteins were washed off with equilibration buffer; bound AAG was eluted with 1M NaCl, 0.13M NaAc pH 4.1. Resin capacities were calculated by dividing total AAG eluted by volume of resin used. The results are shown in Table 1.

Results

TABLE 1

| Resin | AAG binding capacities (mg/ml) |
|---|---|
| DEAE Sephadex A50 (Pharmacia) | 7.9 |
| DEAE Sepharose FF (Pharmacia) | 6.7 |
| Q-Sepharose Big Bead (Pharmacia) | 20.0 |
| Resource Q (Pharmacia) | 8.5 |
| Macro Prep High Q (BioRad) | 3.6 |
| Macro Prep DEAE (BioRad) | 2.6 |
| Toyopearl Super Q (Toso Haas) | 17.0 |
| Poros Q (Perseptive Biosystems) | 4.2 |
| Poros HQ (Perseptive Biosystems) | 5.8 |
| Q Hyper D (F) (Biosepra) | 31.6 |
| Q Hyper D (M) (Biosepra) | 31.5 |

Conclusion

Based on capacity, Q Hyper D, Q Sepharose Big Bead (QSBB) and Toyopearl Super Q had acceptable AAG capacities under the test conditions used.

EXAMPLE 3

Optimisation of Elution Conditions from Anion Exchange Resin

A 1 ml column of QSBB (0.5×5 cm) was equilibrated with 0.13M sodium acetate pH 4.1. A pure preparation of AAG prepared according to Example 1A and then diluted 3 fold with equilibration buffer was loaded onto the column so that it was overloaded. The protein load was followed by a wash of equilibration buffer, so that the UV monitored effluent returned to a baseline recording. A continuous linear salt gradient was applied to the column from 0 to 1M NaCl over 15 column volumes. Elution was continued at the limit concentration for a further 5 column volumes. Eluate was monitored by UV absorbance at 280 nm.

Results

Product elution was initiated by a NaCl concentration of 0.17M. The protein eluted peak coincided with 0.26M NaCl.

Conclusion

When QSBB was loaded with a pure preparation of AAG, it was shown that a suitable buffer containing not less than 0.17M NaCl is required to initiate the elution of bound protein from the column.

EXAMPLE 4

Optimisation of Elution Conditions (continued)

A 1 ml column of QSBB was equilibrated with 0.13M sodium acetate pH 4.1. 5 column volumes of Fraction V supernatant (process start material) was applied to the column. The Fraction V supernatant load was washed through with equilibration buffer, so that the UV monitored effluent returned to a baseline recording. A continuous linear salt gradient was applied to the column over 15 column volumes. The salt gradient was applied from 0 to 0.5M NaCl. The gradient was then stepped to 1M NaCl and maintained for 5 column volumes. Eluate was monitored by UV absorbance at 280 nm.

Results

Product elution was initiated, by a NaCl concentration of 0.13M. Protein eluted peak coincided with 0.15M NaCl.

Conclusion

When QSBB was loaded with Fraction V supernatant, it was shown that a suitable buffer containing not less than 0.13M NaCl is required to initiate the elution of the bound component from the column.

EXAMPLES 5A–B

Confirmation of Elution Conditions

Step gradient elution is the preferred method of elution of process scale chromatography. Examples 3 and 4 have shown that using a linear gradient, a minimum salt concentration of 0.13M NaCl was required to initiate elution of AAG from the column. In a step gradient, to achieve elution in a suitable volume, slightly higher NaCl levels are often needed. The purpose of this experiment was to evaluate the elution properties of 0.2M and 0.3M NaCl to determine the minimum NaCl concentration required for acceptable AAG recovery.

A 1 ml column of QSBB was equilibrated, loaded with Fraction V supernatant, and washed as in Example 4. Step gradient salt elution was applied to the column. After the initial step elution the column was eluted with 1M NaCl to observe if any bound components were eluted.

EXAMPLE 5A

The column was equilibrated, loaded, and washed as above. A step gradient of 0.3M NaCl was applied to the column for 7 bed volumes followed by 5 bed volumes of 1M NaCl.

Results 5A

All of the detectable bound protein was eluted with 0.3M NaCl. No further eluted peak was seen with 1M NaCl.

EXAMPLE 5B

The column was equilibrated, loaded, and washed as above. A step 0.2M NaCl gradient was applied to the column for 7 bed volumes followed by 5 bed volumes of 1M NaCl.

Results 5B

Figure 2:
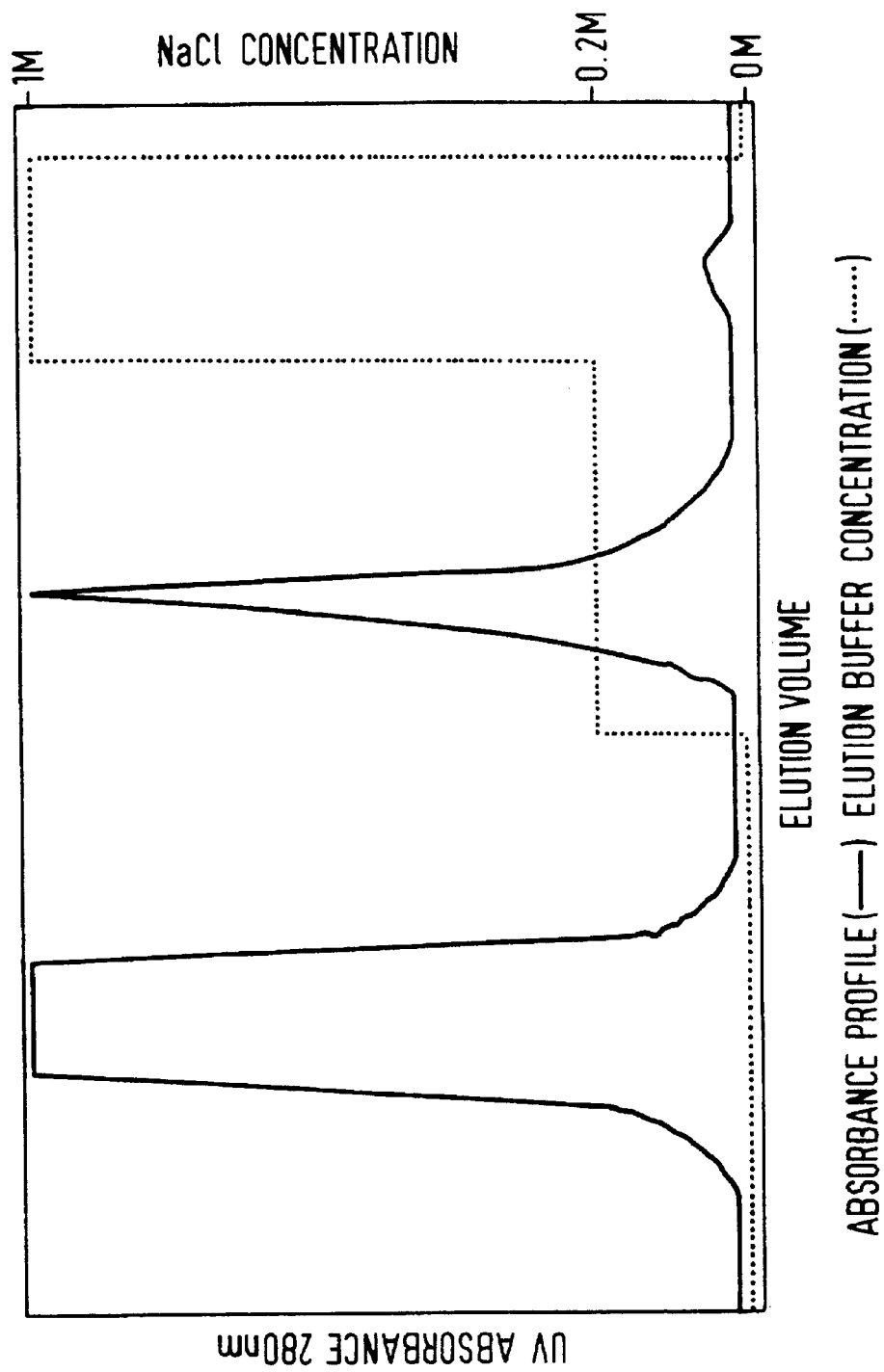
FIG. 2: A diagrammatic representation of a chromatographic profile of a fraction v supernatant applied to a Q sepharose big bead column and eluted with a 0.2M NaCl step gradient.

Of the total bound protein, 96% was eluted with 0.2M NaCl. The remaining bound material was seen to be eluted with 1M NaCl; FIG. 2 shows the chromatographic profile.

Conclusions 5A–B

These results show that a salt concentration of 0.2M to 0.3M NaCl in a suitable buffer is required to provide an acceptable elution of the bound protein.

EXAMPLES 6–7

Demonstration of Effect of Aerosil Treatment Upon Endotoxin Level

Materials

AAG was produced from Fraction V supernatant as previously described in Example 1A.

EXAMPLE 6

An AAG solution at 50 g/l was prepared. This was not Aerosil treated and provided a control reference sample.

EXAMPLE 7

An AAG solution at 50 g/l was treated with 5% w/v Aerosil 380 and stirred at 37° C. for 2 hours.

The products of Examples 6 and 7 were subjected to LAL analysis. The results are shown in Table 2.

TABLE 2

| Example | AAG g/L | Aerosil % w/v | LAL Eu/ml | LAL Eu/mg |
|---------|---------|---------------|-----------|-----------|
| 6 | 50 | 0 | 157 | 3.14 |
| 7 | 50 | 5 | 2.36 | 0.047 |

Conclusions Examples 6–7

The endotoxin activity of an AAG solution at 50 g/l was drastically reduced by Aerosil 380 treatment at 37° C. for 2 hours.

EXAMPLES 8–14

Optimisation of Aerosil Treatment Concentration

EXAMPLE 8

An AAG solution at 50 g/l was prepared as described in Example 1A. This was not Aerosil treated and provided a control reference sample.

EXAMPLE 9

An AAG solution at 50 g/l was treated with 0.1% w/v Aerosil 380 and stirred at 37° C. for 2 hours.

EXAMPLE 10

An AAG solution at 50 g/l was treated with 0.3% w/v Aerosil 380 and stirred at 37° C. for 2 hours.

EXAMPLE 11

An AAG solution at 50 g/l was treated with 0.5% w/v Aerosil 380 and stirred at 37° C. for 2 hours.

EXAMPLE 12

An AAG solution at 50 g/l was treated with 1% w/v Aerosil 380 and stirred at 37° C. for 2 hours.

EXAMPLE 13

An AAG solution at 50 g/l was treated with 3% w/v Aerosil 380 and stirred at 37° C. for 2 hours.

EXAMPLE 14

An AAG solution at 50 g/l was treated with 5% w/v AEROSIL™ fumed silica grade 380 and stirred at 37° C. for 2 hours.

The products of Examples 8 to 14 were subjected to LAL analysis. The results are shown in Table 3.

TABLE 3

| Example | AAG g/L | Aerosil % w/v | LAL EU/ml | Specific Activity EU/mg |
|---|---|---|---|---|
| 8 | 50 | 0 | 25–62.5 | 0.5–1.25 |
| 9 | 50 | 0.1 | 12.5–25 | 0.25–0.5 |
| 10 | 50 | 0.3 | 6.25–12.5 | 0.125–0.25 |
| 11 | 50 | 0.5 | 7.5–12.5 | 0.15–0.25 |
| 12 | 50 | 1 | 7.5–12.5 | 0.15–0.25 |
| 13 | 50 | 3 | 3.75–7.5 | 0:075–0.15 |
| 14 | 50 | 5 | 3.75–7.5 | 0.075–0.15 |

Conclusions Examples 8–14

The clearance of endotoxin activity increased with AEROSIL™ fumed silica grade 380 concentration, with an optimum Aerosil 380 concentration of 3–5% w/v when treating a 50 g/l AAG solution. Optimal endotoxin clearance therefore occurs in the range of 0.6 to 1 g AEROSIL™ fumed silica/g AAG.

EXAMPLES 15–17

Aerosil 380 Treatment at High and Low AAG Concentration Results in Depyrogenation of a Final Product A batch of AAG produced as described in Example 1B as far as stage 1.3 was processed in three aliquots: prior to processing, the AAG concentration was approximately 4 g/l.

EXAMPLE 15

The first aliquot of AAG was concentrated from approximately 4 g/L to approximately 20 g/l by ultrafiltration using membranes with 10,000 molecular weight cut off. This aliquot was not subjected to AEROSIL™ fumed silica grade 380 treatment and provided a control sample.

EXAMPLE 16

The second aliquot was treated with AEROSIL™ fumed silica grade 380 at 1 g:1 g ratio, at 37° C. for 2 hours. The AEROSIL™ fumed silica grade 380 was removed by filtration. The AAG solution was concentrated to 20 g/l by ultrafiltration as in example 15.

EXAMPLE 17

The third aliquot of AAG solution was concentrated from approximately 4 g/L to approximately 20 g/l by ultrafiltration as in example 15. The protein concentrate was AEROSIL™ fumed silica grade 380 treated at 1 g:1 g ratio at 37° C. for 2 hours. The AEROSIL™ fumed silica grade 380 was removed by filtration.

The products from the Examples 15, 16 and 17 were subjected to LAL analysis. Results are shown in Table 4.

TABLE 4

| Example | LAL EU/ml | LAL RU/mg |
|---|---|---|
| 15 | 25–50 | 1–2 |
| 16 | 2.5–5 | 0.103–0.205 |
| 17 | 2.5–5 | 0.123–0.245 |

Conclusions Examples 15–17

The results shown in Table 4, indicate that there is equal clearance of endotoxin, when treatment is at either the dilute or concentrated protein stage.

AEROSIL™ fumed silica grade 380 has a high volume/weight ratio and can occlude a relatively large volume of aqueous solution. Treatment of a dilute protein solution with AEROSIL™ fumed silica at 1 g:1 g ratio reduced the percentage w/v of AEROSIL™ fumed silica. For this reason the loss of product is greatly reduced. Therefore AEROSIL™ fumed silica grade 380 treatment is favoured at the dilute protein stage.

EXAMPLES 18–22

Optimisation of Treatment Time

A solution of AAG produced as described in Example 1A at 50 g/L was treated with AEROSIL™ fumed silica grade 380 at 1 g:1 g ratio, mixing at 37° C. Samples were removed at time intervals and the AEROSIL™ fumed silica grade 380 removed by centrifugation. The supernatant was assayed for presence of endotoxin by LAL analysis. The results are shown in Table 5.

TABLE 5

| Example | Treatment Time mins | LAL EU/ml | Specific Activity Eu/mg |
|---|---|---|---|
| 6 | No treatment | 157 | 3.14 |
| 18 | 0 | 2.89 | 0.058 |
| 19 | 30 | 6.03 | 0.121 |
| 20 | 60 | 4.54 | 0.091 |
| 21 | 90 | 2.31 | 0.046 |
| 22 | 1080 | 5.49 | 0.110 |

Conclusions Examples 18–22

Example 6 provides a control for Examples 18–22. In all cases, Examples 18–22, the endotoxin activity has been reduced. It is significant that regardless of treatment time the degree of endotoxin clearance is of the same order. The treatment time quoted in Table 5 does not include the time for Aerosil 380 removal. The treatment time of 0 minutes, has had an effective Aerosil contact time of up to 20 minutes. However, optimum clearance of endotoxin occurs within this time.

EXAMPLES 23–25

Optimisation of Treatment Temperature

A batch of AAG produced as described in Example 1B was processed in three aliquots.

EXAMPLE 23

The first aliquot of AAG solution at approximately 4.5 g/l was concentrated to 100 g/L by ultrafiltration. This was not AEROSIL™ fumed silica grade 380 treated and provided a control sample.

EXAMPLE 24

The second aliquot of AAG solution at approximately 4.5 g/l was AEROSIL™ fumed silica grade 380 treated at 1 g:1 g ratio at room temperature (RT), about 20° C. for 2 hours. The AEROSIL™ fumed silica grade 380 was removed by filtration and the protein concentrated to 100 g/L by ultrafiltration.

EXAMPLE 25

The third aliquot was processed as in Example 24 but the AEROSIL™ fumed silica grade 380 treatment temperature was 37° C.

Products from examples 23–25 were assayed for endotoxin by LAL analysis. Results are shown in Table 6.

TABLE 6

| Example | Temperature °C. | LAL EU/ml | LAL EU/mg |
|---|---|---|---|
| 23 | Control | 25 | 0.25 |
| 24 | RT | 6.25 | 0.0625 |
| 25 | 37 | 7.50 | 0.0750 |

Conclusions Examples 23–25

AEROSIL™ fumed silica grade 380 treatment at both temperatures significantly reduced the endotoxin activity in the final product compared to the control. It appears there is no significant difference between treatment temperatures on endotoxin clearance.

EXAMPLE 26

Effect of Prolonged Heat on AAG Structure

AAG in PBS pH 7.5 was diluted to 50 g/l then aliquoted into 3×1.5 mls; one of each was incubated in a waterbath for 18 hrs at 60, 65 or 70° C. The preparations were analysed by Gel Permeation Chromatography using a FPLC Superose 12 column (Pharmacia High Resolution 10×300 mm) equilibrated in 0.1M sodium chloride 50 mM Tris (Tris(hydroxymethyl)aminomethane), 0.05% sodium azide pH 7.5 at 0.5 ml/min. The results are shown in Table 7.

Results

TABLE 7

| Temperature of Incubation | % Aggregate | % Dimer | % Monomer |
|---|---|---|---|
| 60° C. | 1 | 3.6 | 94.8 |
| 65° C. | 2.4 | 10.2 | 86.7 |
| 70° C. | 5.8 | 8.8 | 83.5 |
| Control unheated | 0 | 1.2 | 98.5 |

Conclusion

AAG in PBS pH 7.5, without any stabilisers, is stable to prolonged heating at high temperatures. These results indicate that pasteurisation is a feasible viral inactivation method for this product, and further experiments have indicated that the pasteurised products retain full molecular integrity.

EXAMPLE 27

Effect of Stabilizers on Pasteurisation of AAG

Method

AAG in PBS pH 7.5 was mixed with various chemicals which are known to stabilise other plasma proteins. Final protein concentration was adjusted to 50 g/l AAG. All samples, except the control, were heated in a waterbath at 62° C. for 18 hours. On cooling, the samples were assayed by Gel Permeation Chromatography using a FPLC Superose 12 column. The results are shown in Table 8.

TABLE 8

| Stabiliser | 18 hrs at 62° C. | % Aggregate | % Dimer | % Monomer |
|---|---|---|---|---|
| None | − | 0 | 0 | 99.6 |
| None | + | 0 | 3.9 | 95.2 |
| 0.5 M NaCl | + | 0 | 5.5 | 93.9 |
| 1.5 M NaCl | + | 0 | 18.1 | 81.5 |
| 2.5 M NaCl | + | 0 | 42.3 | 57.4 |
| 0.03 M glycine | + | 0 | 4.2 | 94.8 |
| 0.1 M glycine | + | 0 | 4.4 | 94.7 |
| 0.16 M glycine | + | 0 | 4.1 | 94.9 |
| 5% sucrose | + | 0 | 3.0 | 95.3 |
| 20% sucrose | + | 0 | 2.1 | 97.0 |
| 35% sucrose | + | 0 | 1.5 | 97.6 |
| 10 mM Octanoate | + | 0 | 2.8 | 96.4 |
| 30 mM Octanoate | + | 0 | 3.7 | 95.3 |
| 50 mM Octanoate | + | 0 | 5.7 | 93.3 |

Conclusion (comparative)

Increasing NaCl levels above 0.15M appears to have a destabilising effect, more dimer is formed on heating as NaCl is increased. Glycine at 30 to 160 mM appears to have no effect. Sucrose at 5 to 35% has a slight stabilising effect on AAG.

EXAMPLES 28–31 (COMPARATIVE)

Evaluation of Other Methods for Depyrogenation of AAG

EXAMPLE 28

Endotoxin Removal Using Charcoal

Chen, R. F. (Journal of Biological Chemistry, 242 (2) pp 173–181, 1967), described a method for the removal of fatty acids from albumin using activated charcoal. It was conjectured that LPS removal from AAG might be achieved with charcoal on the basis that LPS is known to possess a Lipid A moiety.

Methods

A) 370 mg of Norit GSX activated charcoal was added to 10 mls of AAG solution produced as described in Example 1A at a concentration of 74 g/l. The mixture was adjusted from pH 7.3 to pH 4.0 by the addition of 0.2M HCl. The mixture was stirred in an ice bath for 1 hour. The bulk of the charcoal was removed by centrifugation at 2000 g for 15 minutes. The supernatant was decanted and filtered through 0.8 μm and 0.2 μm membrane filters in series. The solution was pH adjusted with 0.2M NaOH to a final pH of 7.1. The sample was then subjected to LAL analysis.

B) Following the same principle of removing endotoxin with charcoal, the effectiveness of charcoal impregnated filters was evaluated.

Charcoal impregnated 47 mm filters, grade R53 SLP were supplied by Cuno Process Filtration. The filter was flushed with 50 mls of pyrogen free water (PFW). A sample of the water flush was taken. 30 mls of AAG solution produced as described in Example 1A at a concentration of 74 g/l was passed slowly through the filter to maximise the contact time. 5×5 ml filtrate samples were collected. The 5 filtrate samples along with an unfiltered control and the filter water flush were subjected to LAL analysis.

Results

Results of LAL analysis of samples produced in Example 28 are displayed in Table 9.

TABLE 9

Charcoal Treatments

| Sample | Treatment | Stage | Protein Concentration mg/ml | LAL Eu/ml | LAL Eu/mg |
|---|---|---|---|---|---|
| AAG (as in 1A) | Charcoal | Control | 74.15 | 271 | 3.65 |
|  |  | Post treated | 74.15 | 150 | 2.02 |
| AAG (as in Example 1A) | Cuno Charcoal filters | Control | 74.15 | 271 | 3.65 |
|  |  | PFW Filter Flush | 0 | 0.123 | ~ |
|  |  | Filtrate 1 | Not Tested | 16.5* | Not Calculated |
|  |  | Filtrate 2 |  | 138 |  |
|  |  | Filtrate 3 |  | 217 |  |
|  |  | Filtrate 4 |  | 217 |  |
|  |  | Filtrate 5 |  | 262 |  |

*residual PFW from filter flush

Conclusions 28

The results of the LAL analysis indicate no significant decrease in endotoxin by either of the charcoal treatment methods.

EXAMPLE 29

Endotoxin Removal Using Affinity Ligands

Two kits, PyroBind (Sepracor) and END-XB15 (Atlas Bioscan Ltd.), specifically designed for endotoxin removal from aqueous protein solutions were evaluated. Both kits consist of a specific ligand, Endotoxin Neutralising Protein (ENP), coupled to rigid support. END-X B15 beads are 65 μm silica spheres coated with ENP. PyroBind™ is a hollow fibre support with coupled ENP.

END-X B15

The manufacturers protocol was followed. An AAG solution produced as described in Example 1A was diluted to a concentration of 20 g/l. 2 mls of the diluted AAG solution was filled into a microcentrifuge tube containing the END-X B15 beads. The solution was end over end mixed for 6 hours at room temperature. At 1, 4 and 6 hours the treatment tube was microcentrifuged at 1000 g to pellet the END-X beads and a 0.5 ml sample removed. The beads were then resuspended and the treatment continued. The time course samples along with a non-treated control were subjected to LAL analysis.

PyroBind

The manufacturers protocol was followed. An AAG solution produced as described in Example 1A at a concentration of 100 g/l was used. A second aliquot of the same solution was diluted to 20 g/l. A syringe containing 5 mls of the 20 g/l AAG was connected to one end of the hollow fibre PyroBind unit and an empty syringe to the other end. The AAG solution was passed through the unit from one syringe to the other 5 times. 5 mls of AAG at 100 g/l was treated in the same way, but the solution was passed through the PyroBind unit 10 times. The solutions were then subjected to LAL analysis along with non-treated control samples.

A further modified protocol was also evaluated. 6 mls of an AAG solution at a concentration of 20 g/l produced as above was subjected to 5 passes through a PyroBind unit. 3 mls of the primary treated AAG was retained. The remaining 3 mls was subjected to a further 5 passes through a second PyroBind unit. Both primary and secondary treated samples along with a non-treated control sample were subjected to LAL analysis.

A control experiment using Human Albumin Solution (ZENALB™ human albumin product 4.5, BioProcess Laboratories) was performed to show the PyroBind units were active. The albumin solution was diluted to a concentration of 22.5 g/l with pyrogen free water (PFW). *Escherichia coli* control standard endotoxin #0113, PPE-E-434 (Associate of Cape Cod Inc.), was reconstituted with PFW. 0.1 ml of the endotoxin standard was added to 5 mls of albumin, mixed and passed through a PyroBind hollow fibre unit 5 times. The treated and non treated samples were subjected to LAL analysis.

Results

Results of LAL analysis of samples produced in Example 29 are displayed in Table 10.

Conclusions

The control albumin sample showed that the PyroBind units successfully removed 98% of the endotoxin with 5 passes through the unit. Using the PyroBind unit to remove endotoxin from AAG solutions showed at best only a 53% reduction in endotoxin. Results for END-X B15 were similar to PyroBind giving only a 59% reduction in endotoxin after 6 hours treatment. Neither of the kits met the manufacturers claims when treating AAG solutions and would not therefore be suitable for producing a clinical grade preparation.

TABLE 10

Evaluation of PyroBind

| Sample | Treatment | Stage | Protein Concentration mg/ml | LAL Eu/ml | Actual EU Reduction | % EU Reduction | LAL Eu/mg |
|---|---|---|---|---|---|---|---|
| AAG (as in Example 1A) | PyroBind 5 unit passes | Control | 100 | 88.8 | 13.60 | 15 | 0.89 |
|  |  | Treated | 100 | 75.2 |  |  | 0.75 |
|  |  | Control | 20 | 15.1 | 5.47 | 36 | 0.75 |
|  |  | Treated | 20 | 9.6 |  |  | 0.48 |
| AAG (as in Example 1A) | PyroBind 5 passes *2 units | Control | 20 | 12.5 | 3.05 | 24 | 0.63 |
|  |  | 1st Unit | 20 | 9.5 | 6.63 | 53 | 0.47 |
|  |  | 2nd Unit | 20 | 5.9 |  |  | 0.29 |
| Albumin ADA0407 | PyroBind | Control | 22.5 | 9.3 | 9.1 | 98 | 0.41 |
|  |  | Treated | 22.5 | 0.2 |  |  | 0.01 |

EXAMPLE 30

Ion Exchange Chromatography

Pyrogens have low pI; published values vary, most quote approximately 4 and some much lower. Hence for many proteins e.g. albumin pI=4.7, depyrogenation can be achieved by anion exchange chromatography. For AAG having a pI of 2.7 this technique has less potential. In preliminary experiments AAG was flowed through an anion exchanger under non-binding conditions for AAG, to try to bind pyrogens.

A 25 mls column of DEAE Sepharose FF (Pharmacia) (1.6×12.5 cm) was depyrogenated with 250 mls 0.5M NaOH then equilibrated with 250 mls 0.13M sodium acetate pH 4.1. AAG prepared as in Example 1A was taken, solid NaCl added to increase NaCl concentration to 0.2M; 130 mls of this preparation at an AAG concentration of 19 g/l, and pH 4.4 was loaded onto the anion exchanger; the flow through fraction was collected into a depyrogenated container. The flow-through fraction and AAG starting material were adjusted to pH 7 then subjected to LAL assay.
Results
Pyrogen levels were only marginally reduced from 25–30 EU/ml to 20–25 EU/ml.
Conclusion
This method did not significantly reduce the pyrogen level of the AAG preparation.

EXAMPLE 31

Endotoxin Removal Using Amberlite XAD-2

Amberlite XAD-2 resin is a synthetic polystyrene polymer without ionic groups designed for adsorbing water soluble organic substrates; it has been used for depyrogenating water.

AAG was produced as described in Example 1A and diluted to 50 g/l. 1 g of unwashed, unequilibrated Amberlite XAD-2 resin was added to 4 mls of AAG solution. The mixture was shaken at 37° C. for 2 hours. The Amberlite was removed by centrifugation at 1000 g for 20 minutes. Non-pelleted resin was removed by filtration. Samples of pre- and post-treated AAG were subjected to LAL analysis.
Results 31
Results of LAL analysis of sample produced in Example 31 are displayed in Table 11.

TABLE 11

| Sample | LAL EU/ml | LAL EU/mg |
|---|---|---|
| Pre-treated AAG | 157 | 3.14 |
| Post-treated AAG | 164 | 3.28 |

Conclusions 31
A reduction in endotoxin level using Amberlite XAD-2 resin was not achieved and therefore the method was considered unsuitable as an AAG treatment method.

What is claimed is:

1. A method of removing lipopolysaccharide (LPS) from an alpha-1-acid glycoprotein (AAG) containing preparation comprising contacting said preparation with a finely divided inorganic non-toxic resin, to produce an AAG preparation having a LPS concentration of less than or equal to 0.1 Eu/mg AAG.

2. A method as claimed in claim 1 wherein the resin is a non-substituted resin.

3. A method as claimed in claim 1 wherein the resin is a particulate resin.

4. A method as claimed in claim 1 wherein the resin is a hydrophilic resin.

5. A method as claimed in claim 1 wherein the resin is silane-based.

6. A method as claimed in claim 1 wherein the resin comprises fumed silica.

7. A method of purifying AAG comprising contacting an AAG-containing preparation with an anion exchange matrix, eluting an AAG-enriched fraction from said matrix and depyrogenating an AAG-enriched fraction by contact with a finely divided inorganic non-toxic particulate resin followed by separation of an LPS-depleted AAG fraction, to produce an AAG preparation having a LPS concentration of less than or equal to 0.1Eu/mg AAG.

8. A method as claimed in claim 7 wherein the AAG containing preparation is Cohn Fraction V supernatant.

9. A method as claimed in claim 7 wherein the AAG containing preparation is contacted with the anion exchange matrix in the presence of a 30 to 45% ethanolic solution.

10. A method as claimed in claim 7 wherein the AAG containing material:anion exchange matrix ratio is from 1000:1 to 5:1.

11. A method as claimed in claim 7 wherein the eluted AAG enriched preparation is neutralized prior to depyrogeneration.

12. A method as claimed in claim 7 wherein the ratio of finely divided non-toxic resin to AAG protein is from 50:1 to 0.2:1 (w/w).

13. A method as claimed in claim 7 wherein in the depyrogenation step the AAG concentration in solution is from 0.1 to 250 g/L.

14. A method as claimed in claim 7 wherein the depyrogenated AAG is concentrated.

15. A method as claimed in claim 7 which additionally comprises a virus inactivation step.

16. A method as claimed in claim 15 wherein the virus inactivation step comprises pasteurization.

17. A method as claimed in claim 15 wherein the virus inactivation step comprises filtration.

* * * * *